US012763193B2

(12) United States Patent
Prakash et al.

(10) Patent No.: US 12,763,193 B2
(45) Date of Patent: Oct. 13, 2026

(54) GENERATING GROUND TRUTH ANNOTATED DATASET FOR ANALYSING MEDICAL IMAGES

(71) Applicant: PSIP2 LLC, Manchester, NH (US)

(72) Inventors: Prithvi Prakash, Bangalore (IN); Warsha Barde, Bangalore (IN); Harish Doraiswamy, Bangalore (IN); Nithin Shivshankar, Bangalore (IN); S Raghu Menon, Bangalore (IN); Shanthanu Chakravarthy, Bangalore (IN)

(73) Assignee: PSIP2 LLC, Manchester, NH (US)

( * ) Notice: Subject to any disclaimer, the term of this patent is extended or adjusted under 35 U.S.C. 154(b) by 218 days.

(21) Appl. No.: 18/395,017

(22) Filed: Dec. 22, 2023

(65) Prior Publication Data

US 2024/0257946 A1 Aug. 1, 2024

Related U.S. Application Data

(63) Continuation-in-part of application No. PCT/IN2022/050547, filed on Jun. 15, 2022.

(30) Foreign Application Priority Data

Jun. 23, 2021 (IN) ............................. 202141028259

(51) Int. Cl.
*G16H 30/40* (2018.01)
*G06N 3/0455* (2023.01)
(Continued)

(52) U.S. Cl.
CPC ........... *G16H 30/40* (2018.01); *G06N 3/0455* (2023.01); *G06N 3/0464* (2023.01); *G06N 3/09* (2023.01);
(Continued)

(58) Field of Classification Search
CPC ......... G16H 30/40; G06T 7/0012; G06T 7/10; G06T 7/11; G06T 7/194;
(Continued)

(56) References Cited

U.S. PATENT DOCUMENTS 9,280,819 B2 3/2016 Codella
10,430,946 B1 * 10/2019 Zhou .................. A61B 5/02007
(Continued)

FOREIGN PATENT DOCUMENTS

EP 3760125 1/2021
WO WO2020/183230 A1 9/2020
WO WO-2022223922 A1 * 10/2022 ............... G06T 7/11

OTHER PUBLICATIONS

Serdjebi et al.—Machine Translation of WO 2022/223922—Oct. 27, 2022 (Year: 2022).*
(Continued)

*Primary Examiner* — Jennifer Mehmood
*Assistant Examiner* — Jose M Torres
(74) *Attorney, Agent, or Firm* — Bond, Schoeneck & King, PLLC

(57) ABSTRACT

A method for semi-automatically generating annotated data-set for machine learning implementation for segmenting lesions in medical images. The method comprises utilizing a trained segmentation model to generate a first segmentation mask for each of the one or more lesions in medical images; implementing a geometric filter to validate the generated first segmentation mask; updating the trained segmentation model with the validated first segmentation mask; implementing the updated segmentation model to generate a second segmentation mask for each of the one or more lesions in the medical images; providing a user interface to allow an operator to validate last generated segmentation mask; and selecting the medical images with the
(Continued)

validated generated segmentation mask, to generate a ground truth annotated dataset.

18 Claims, 12 Drawing Sheets

(51) Int. Cl.

| | |
|---|---|
| ***G06N 3/0464*** | (2023.01) |
| ***G06N 3/09*** | (2023.01) |
| ***G06T 7/00*** | (2017.01) |
| ***G06T 7/10*** | (2017.01) |
| ***G06T 7/11*** | (2017.01) |
| ***G06T 7/194*** | (2017.01) |

(52) U.S. Cl.
CPC .............. *G06T 7/0012* (2013.01); *G06T 7/10* (2017.01); *G06T 7/11* (2017.01); *G06T 7/194* (2017.01); *G06T 2207/10068* (2013.01); *G06T 2207/20024* (2013.01); *G06T 2207/20081* (2013.01); *G06T 2207/20084* (2013.01); *G06T 2207/30032* (2013.01); *G06T 2207/30096* (2013.01)

(58) Field of Classification Search
CPC . G06T 2207/10068; G06T 2207/20024; G06T 2207/20081; G06T 2207/20084; G06T 2207/30032; G06T 2207/30096; G06N 3/09; G06N 3/0455; G06N 3/0464
See application file for complete search history.

(56) References Cited

U.S. PATENT DOCUMENTS

| | | | | |
|---|---|---|---|---|
| 2010/0260390 | A1* | 10/2010 | Liang | G06V 10/25 382/128 |
| 2011/0158491 | A1* | 6/2011 | Markova | G06T 7/41 382/128 |
| 2011/0216951 | A1* | 9/2011 | Ye | G06T 7/143 382/128 |
| 2011/0229004 | A1* | 9/2011 | Buelow | G06T 7/0012 382/131 |
| 2019/0172581 | A1* | 6/2019 | Zlotnick | G16H 50/20 |
| 2019/0198156 | A1 | 6/2019 | Madani | |
| 2020/0085382 | A1* | 3/2020 | Taerum | A61B 5/055 |
| 2020/0160520 | A1 | 5/2020 | Prosky | |
| 2020/0311913 | A1 | 10/2020 | Soni | |
| 2021/0110196 | A1 | 4/2021 | Syeda-Mahmood | |
| 2021/0327068 | A1* | 10/2021 | Joskowicz | G06T 7/0016 |
| 2022/0189028 | A1* | 6/2022 | Yoo | G16H 50/50 |
| 2022/0301156 | A1* | 9/2022 | Fang | G16H 50/70 |
| 2022/0319008 | A1* | 10/2022 | Bengtsson | G06T 7/0016 |
| 2023/0281809 | A1* | 9/2023 | Song | G06N 3/096 382/131 |

OTHER PUBLICATIONS

PCT/IN2022/050547, Search Report and Written Opinion (Sep. 16, 2022).

* cited by examiner

300

GENERATING GROUND TRUTH ANNOTATED DATASET FOR ANALYSING MEDICAL IMAGES

This application is a continuation-in-part of International application Ser. No. PCT/IN2022/050547, filed Jun. 15, 2022, System and Method for Generating Ground Truth Annotated Dataset for Analysing Medical Images, and claims priority from India Patent App. 202141028259, filed Jun. 23, 2021, System and Method for Generating Ground Truth Annotated Dataset for Analysing Medical Images. The entire disclosure of the parent application(s) is/are incorporated herein by reference.

BACKGROUND

The present disclosure generally relates to the field of medical diagnosis by computer-aided analysis of medical images, and more particularly to a system and a method for semi-automatically generating ground truth annotated dataset for machine learning implementation for segmenting lesions in medical images.

In the early stages of medical conditions, like various types of cancers, many patients experience few or no symptoms. Because the lack of symptoms makes such cancers difficult to detect, thus medical personnel are often only able to diagnose such cancerous disease at more advanced stages, and by that point it may get very challenging to treat. That said, in case of some cancers, for instance colorectal cancer, which is the third most frequently diagnosed cancer and the second leading cause of cancer death worldwide, the risk of developing colorectal cancer can be significantly reduced through early diagnosis of polyps during a colonoscopy by analysing correspondingly generated medical images. However, in the field of medical imaging, the segmentation of abnormal anatomical structures or lesions such as gastrointestinal polyps, aneurisms or lung nodules in many cases, are possible precursors to cancers) is a challenging problem because of their highly variable shape, texture, density and size and their attachment to surrounding normal structures.

Currently, endoscopy screenings are the standard for detection and localization of such abnormal tissue regions and precancerous lesions. The success of the diagnosis depends highly on the operator's experience and skills, both for dexterous manoeuvring of the camera and for ensuring full exploration of the mucosa. Such screenings are manual procedures performed by physicians and are therefore affected by human factors like fatigue, lack of sensitivity to visual characteristics of lesions or insufficient attentiveness during examination. Therefore, there is a significant miss rate for these suspicious lesions. For example, some studies suggest a miss rate of 8% to 37%. This can be potentially attenuated by detecting and localizing polyps accurately.

Computer aided diagnosis of diseases has become important to such fields as cardiology, radiology, and other areas of medicine. These have the benefit of images or time dependent signals. With the advent of deep learning in recent years, the ability of computers to perform vision tasks such as identification, localisation and generation has seen success. More specifically, Convolutional Neural Networks (CNNs) have proven particularly effective towards the task of image segmentation and therefore can be leveraged to solve lesion segmentation tasks in medical space with applications in endoscopic, MRI, CT and X-ray images among several others. Ideally, a real-time automatic pixel wise lesion-segmentation system could serve as an effective second observer that could draw the doctor's attention, in real time, to concerning lesions, effectively creating a 'second set of eyes' on all aspects of the video data with fidelity.

However, development of such a system requires training a machine learning model on a large volume of ground truth annotated data which is usually cited as a bottleneck because of its time and labour-intensive nature. Moreover, existing deep learning models trained on publicly available data sets do not retain their performance when used on data locally sourced from different hospitals, and requires incorporating annotated images from the new data source into the training scheme.

Therefore, there exists a need to overcome the bottleneck of generating annotated dataset for machine learning model for segmenting lesions in medical images. The present disclosure has been made in view of such considerations, and it is an object of the present disclosure to provide systems and methods for generating ground truth annotated dataset for machine learning implementation for segmenting lesions in medical images to overcome the limitations of the prior-art.

SUMMARY

The present disclosure overcome the bottleneck of generating annotated dataset for machine learning models for segmenting lesions in medical images by employing computational geometric techniques to automate the generation of ground truth, thus reducing the expert's efforts to answering yes/no questions or selecting the best option from a set of prospective options, thereby reducing time and effort. This ground truth annotated data is then fed back to the geometric filter and the model for their further refinement and fine-tuning.

In an aspect, the present disclosure provides a method for semi-automatically generating annotated dataset for machine learning implementation for segmenting lesions in medical images. The method comprises receiving a plurality of medical images, with a set of medical images of the plurality of medical images being categorized into positive images having one or more lesions. The method further comprises utilizing a trained segmentation model to generate a first segmentation mask for each of the one or more lesions in each of the medical images in the set of medical images. The method further comprises implementing a geometric filter to validate if the generated first segmentation mask corresponds to the one or more lesions in the corresponding medical image based on geometric properties of the respective one or more lesions. The method further comprises updating the trained segmentation model using medical images with the validated first segmentation mask to obtain an updated segmentation model. The method further comprises implementing the updated segmentation model to generate a second segmentation mask for each of the one or more lesions in the medical images in the set of medical images. The method further comprises providing a user interface to allow an operator to validate last generated segmentation mask for each of the medical images in the set of medical images. The method further comprises selecting the medical images from the plurality of medical images with the validated generated segmentation mask, to generate a ground truth annotated dataset.

In one or more embodiments, the method further comprises providing a user interface to allow an operator to classify each of the received plurality of medical images into one of: single lesion image with only one lesion, multiple lesions image with at least two lesions, normal image with no lesions and unclear image, and wherein the medical images being classified as at least one of the single lesion image and the multiple lesions image are categorized as the positive images.

In one or more embodiments, in case of the medical image being classified as the multiple lesions image, the method further comprises: providing a user interface to an operator to outline a bounding polygon on each of at least two lesions in the multiple lesions image; configuring the trained segmentation model to generate a sub-segmentation mask for each of the at least two lesions in the multiple lesions image; and generating the segmentation mask for the multiple lesions image by union of the corresponding generated sub-segmentation masks.

In one or more embodiments, the step of implementing the geometric filter comprises one or more of, two or more of:

- determining an area fraction based on a ratio of an area covered by one of the lesions or its segmentation mask to a total area covered by other of one or more lesions or all lesions of the containing medical image;
- a relative area fraction based on a ratio of an area covered by one of the lesions or its segmentation mask to a total area covered by a largest component of other of one or more lesions or segmentation masks of the containing medical image;
- a convexity based on a ratio of an area covered by a lesions or its segmentation mask to an area of a convex hull of the lesion or segmentation mask;
- an elliptical aspect ratio based on a ratio of major axis to minor axis of an ellipse corresponding a lesion or segmentation mask; and
- an elliptical proximity based on a ratio of a major and minor axis for an ellipse that circumscribes the lesion or its segmentation mask, or a ratio of a perimeter of an elliptical structure with same area as an ellipse corresponding to each of the one or more lesions with major axis and minor axis thereof being equal to length and width respectively of a minimum bounding rectangle thereto in the corresponding medical image, to a perimeter of the ellipse corresponding to each of the one or more lesions in the corresponding medical image, for each of the plurality of medical images.

In one or more embodiments, the method further comprises: configuring the geometric filter to discard the medical image if the corresponding determined area fraction is less than a predefined threshold; and implementing a regression function, trained based on ground truth values for relative area fraction, convexity, elliptical aspect ratio and elliptical proximity for lesions in medical images, to validate if the generated segmentation mask corresponds to the one or more lesions in the corresponding medical image of the plurality of medical images based on the determined relative area fraction, the determined convexity, the determined elliptical aspect ratio, and the determined elliptical proximity for lesions in the corresponding medical image.

In one or more embodiments, the method further comprises varying one or more weighted parameters of the implemented regression function to manipulate validation of the generated segmentation mask.

In one or more embodiments, the method further comprises augmenting a number of medical images in the plurality of medical images by using one or more techniques of: rotate, width-shift, horizontal-shift, horizontal-flip, vertical-flip, zoom, brightness and shear.

In one or more embodiments, providing the user interface comprises configuring the user interface to allow the operator to confirm one of the first segmentation mask and the last generated segmentation mask by using a single action.

In another aspect, the present disclosure provides a system for semi-automatically generating annotated dataset for machine learning implementation for segmenting lesions in medical images. The system comprises a memory arrangement configured to receive a plurality of medical images corresponding to regions with possible one or more lesions, with a set of medical images of the plurality of medical images being categorized into positive images having one or more lesions. The system further comprises a processing arrangement configured to: utilize a trained segmentation model to generate a first segmentation mask for each of the one or more lesions in each of the medical images in the set of medical images; implement a geometric filter to validate if the generated first segmentation mask corresponds to the one or more lesions in the corresponding medical image based on geometric properties of the respective one or more lesions; update the trained segmentation model using medical images with the validated first segmentation mask to obtain an updated segmentation model; implement the updated segmentation model to generate a second segmentation mask for each of the one or more lesions in the medical images in the set of medical images; provide a user interface to allow an operator to validate last generated segmentation mask for each of the medical images in the set of medical images; and select the medical images from the plurality of medical images with the validated generated segmentation mask, to generate a ground truth annotated dataset.

The foregoing summary is illustrative only and is not intended to be in any way limiting. In addition to the illustrative aspects, embodiments, and features described above, further aspects, embodiments, and features will become apparent by reference to the drawings and the following detailed description.

DESCRIPTION OF THE DRAWINGS

For a more complete understanding of example embodiments of the present disclosure, reference is now made to the following descriptions taken in connection with the accompanying drawings in which.

DESCRIPTION

Figure 1:
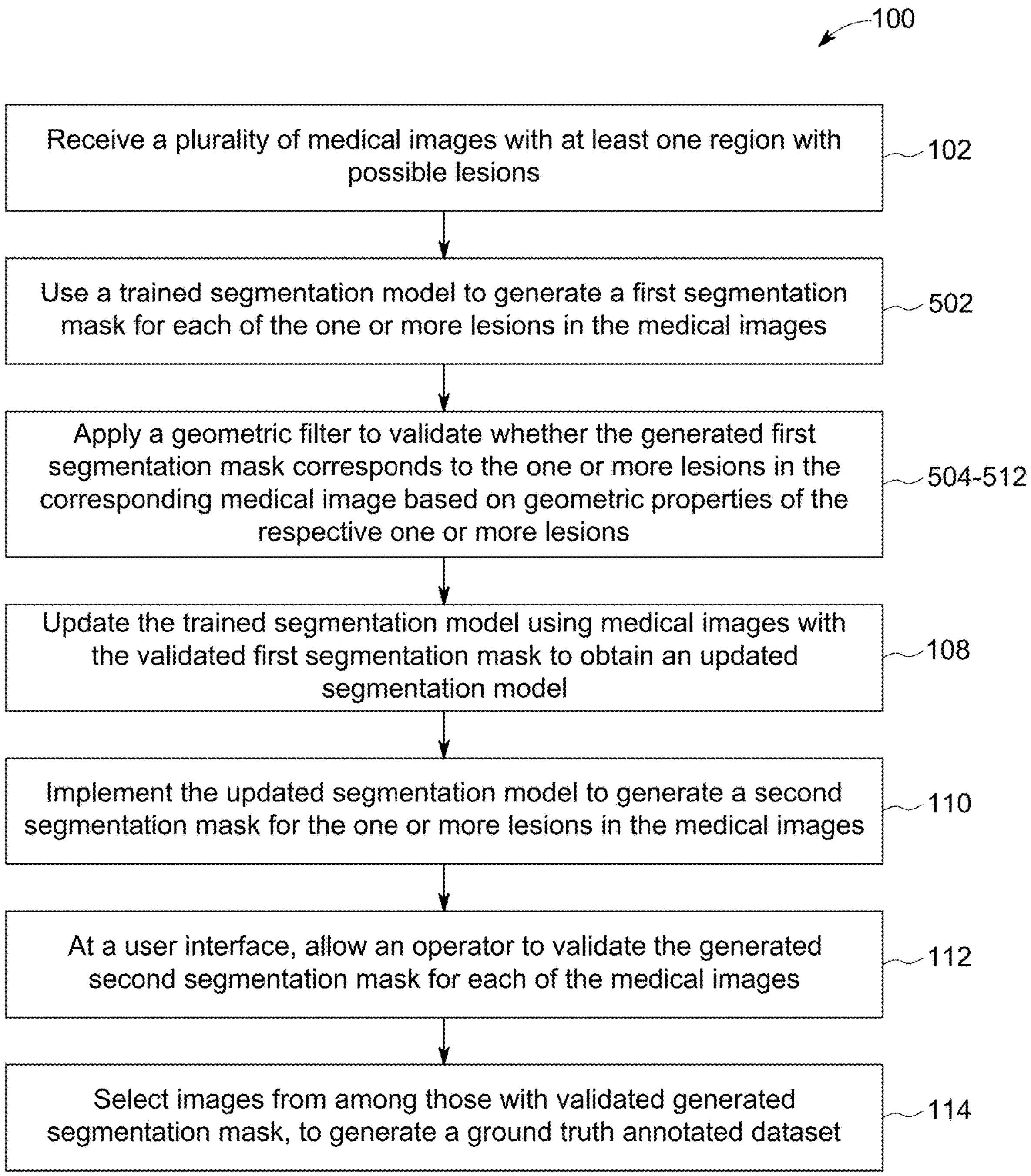
FIG. 1 illustrates a flowchart listing steps involved in a method for semi-automatically generating annotated dataset for machine learning implementation for segmenting lesions in medical images, in accordance with one or more exemplary embodiments of the present disclosure.

The Description is organized as follows.

I. Definitions and computer implementation
II. Identifying and localizing polyps via machine learning
III. Geometric filter
IV. Validation and retraining of the model

I. Definitions and Computer Implementation

In the following description, for purposes of explanation, numerous specific details are set forth in order to provide a thorough understanding of the present disclosure. It will be apparent, however, to one skilled in the art that the present disclosure is not limited to these specific details.

Reference in this specification to "one embodiment" or "an embodiment" means that a particular feature, structure, or characteristic described in connection with the embodiment is included in at least one embodiment of the present disclosure. The appearance of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer-readable storage media and communication media; non-transitory computer-readable media include all computer-readable media except for a transitory, propagating signal. Generally, program modules include routines, programs, objects, components, data structures, etc., that perform particular tasks or implement particular abstract data types. The functionality of the program modules may be combined or distributed as desired in various embodiments.

Some portions of the detailed description that follows are presented and discussed in terms of a process or method. Although steps and sequencing thereof are disclosed in figures herein describing the operations of this method, such steps and sequencing are exemplary. Embodiments are well suited to performing various other steps or variations of the steps recited in the flowchart of the figure herein, and in a sequence other than that depicted and described herein. Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

In some implementations, any suitable computer usable or computer readable medium (or media) may be utilized. The computer readable medium may be a computer readable signal medium or a computer readable storage medium. The computer-usable, or computer-readable, storage medium (including a storage device associated with a computing device) may be, for example, but is not limited to, an electronic, magnetic, optical, electromagnetic, infrared, or semiconductor system, apparatus, device, or any suitable combination of the foregoing. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fibre, a portable compact disc read-only memory (CD-ROM), an optical storage device, a digital versatile disk (DVD), a static random access memory (SRAM), a memory stick, a floppy disk, a mechanically encoded device such as punch-cards or raised structures in a groove having instructions recorded thereon, a media such as those supporting the internet or an intranet, or a magnetic storage device. Note that the computer-usable or computer-readable medium could even be a suitable medium upon which the program is stored, scanned, compiled, interpreted, or otherwise processed in a suitable manner, if necessary, and then stored in a computer memory. In the context of the present disclosure, a computer-usable or computer-readable, storage medium may be any tangible medium that can contain or store a program for use by or in connection with the instruction execution system, apparatus, or device.

In some implementations, a computer readable signal medium may include a propagated data signal with computer readable program code embodied therein, for example, in baseband or as part of a carrier wave. In some implementations, such a propagated signal may take any of a variety of forms, including, but not limited to, electro-magnetic, optical, or any suitable combination thereof. In some implementations, the computer readable program code may be transmitted using any appropriate medium, including but not limited to the internet, wireline, optical fibre cable, RF, etc. In some implementations, a computer readable signal medium may be any computer readable medium that is not a computer readable storage medium and that can communicate, propagate, or transport a program for use by or in connection with an instruction execution system, apparatus, or device.

In some implementations, computer program code for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java®, Smalltalk, C++ or the like. Java and all Java-based trademarks and logos are trademarks or registered trademarks of Oracle and/or its affiliates. However, the computer program code for carrying out operations of the present disclosure may also be written in conventional procedural programming languages, such as the "C" programming language, PASCAL, or similar programming languages, as well as in scripting languages such as JavaScript, PERL, or Python. In present implementations, the used language for training may be one of Python, Tensorflow™, Bazel, C, C++. Further, decoder in user device (as will be discussed) may use C, C++ or any processor specific ISA. Furthermore, assembly code inside C/C++ may be utilized for specific operation. Also, ASR (automatic speech recognition) and G2P decoder along with entire user system can be run in embedded Linux (any distribution), Android, iOS, Windows, or the like, without any limitations. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the internet using an Internet Service Provider). In some implementations, electronic circuitry including, for example, programmable logic circuitry, field-programmable gate arrays (FP-GAs) or other hardware accelerators, micro-controller units (MCUs), or programmable logic arrays (PLAs) may execute the computer readable program instructions/code by utilizing state information of the computer readable program instructions to personalize the electronic circuitry, in order to perform aspects of the present disclosure.

In some implementations, the flowchart and block diagrams in the figures illustrate the architecture, functionality, and operation of possible implementations of apparatus (systems), methods and computer program products according to various implementations of the present disclosure. Each block in the flowchart and/or block diagrams, and combinations of blocks in the flowchart and/or block diagrams, may represent a module, segment, or portion of code, which comprises one or more executable computer program instructions for implementing the specified logical function(s)/act(s). These computer program instructions may be provided to a processor of a general purpose computer, special purpose computer, or other programmable data processing apparatus to produce a machine, such that the computer program instructions, which may execute via the processor of the computer or other programmable data processing apparatus, create the ability to implement one or more of the functions/acts specified in the flowchart and/or block diagram block or blocks or combinations thereof. It should be noted that, in some implementations, the functions noted in the block(s) may occur out of the order noted in the figures. For example, two blocks shown in succession may, in fact, be executed substantially concurrently, or the blocks may sometimes be executed in the reverse order, depending upon the functionality involved.

In some implementations, these computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks or combinations thereof.

In some implementations, the computer program instructions may also be loaded onto a computer or other programmable data processing apparatus to cause a series of operational steps to be performed (not necessarily in a particular order) on the computer or other programmable apparatus to produce a computer implemented process such that the instructions which execute on the computer or other programmable apparatus provide steps for implementing the functions/acts (not necessarily in a particular order) specified in the flowchart and/or block diagram block or blocks or combinations thereof.

Referring to FIG. 1, illustrated is a flowchart of a method 100 for semi-automatically generating annotated dataset for machine learning implementation for segmenting lesions in medical images, in accordance with one or more embodiments of the present disclosure. A medical image may be captured using ultrasound waves, an X-ray, high-frequency waves, or the like. Here, the 'object' may be understood to be part of a human body. For example, the object may be an organ of a human body, such as the liver, the heart, the womb, a brain, the breast, or the abdomen, or a foetus. A medical image may be collected and recorded by colonoscope, endoscope, MRI, or any other type of modality and relating to a patient. With the present semi-automatic approach, the medical images may need to be reviewed by a human operator. The medical images may be viewed by a medical image viewer which may broadly refer to any device that can be used to view and/or manipulate medical image data. Examples of medical image viewers include, but are not limited to, dedicated workstation (i.e., image review stations), general-purpose computers, personal digital assistants, cell phones, and set-top boxes. A medical image viewer can also be a medical imaging system (e.g., an ultrasound system) different from the one used to generate the medical image data.

As discussed, the present disclosure pertains to medical diagnosis, and in particular to aid in the process of detection of lesions in the medical images. A lesion may be an area of abnormal growth in an organ which has suffered damage through disease, such as polyps, tumour, melanin, and other abnormal growths. In particular, the present disclosure caters to lesions or abnormalities with well-defined geometry, such as, but not limited to, polyps. One form of lesion is a polyp, an abnormal biological mass that is projecting from a mucous membrane. Generally, a polyp may be in the form of a mass of tissue that bulges or projects outward or upward from the normal surface level, thereby being macroscopically visible as a hemispheroidal, spheroidal, or regular mound-like structure growing from a relatively broad base or a slender stalk. Polyps may be found in a number of tissues, including but not limited to colon, stomach, nose, car, sinus(es), urinary bladder, and uterus. Examples include colon, rectal and nasal polyps. If it is attached to the surface by a long and narrow handle, then it is called a pedunculated polyp; and if there is no handle, then it is called a sessile polyp.

II. Identifying and Localizing Polyps Via Machine Learning

Several machine learning approaches have been proposed for identifying and localizing polyps in endoscopy images. However, these models' ability to perform is constrained by the quality and the variety within the data. While the model can be improved by training it using segmented images from varying sources, this task is time consuming, requiring several minutes even for a single image. This difficulty is corroborated by the fact that crowdsourcing platforms are very expensive for such tasks compared to performing simpler annotations. Thus, given both the cognitive load of this task, as well as the time constraints imposed on the medical experts, it becomes impractical to generate usable training data for each such data source.

A semi-automated approach may be capable of generating high-quality segmentation maps required for training the necessary models while also reducing the burden on the experts. The key idea is to make use of the typical shapes of polyps in conjunction with existing models that are trained on publicly available data to first generate a candidate set of annotations. The final annotated images are then chosen by the experts from among this candidate set using a visual interface that involves answering a simple multiple-choice questionnaire or the like.

In FIG. 1, at step 102, the method 100 comprises receiving a plurality of medical images corresponding to at least one region with possible one or more lesions, with a set of medical images of the plurality of medical images being categorized into positive images having one or more lesions. In one or more embodiments, the method 100 further augmenting a number of medical images in the plurality of medical images by using one or more techniques of: rotate, width-shift, horizontal-shift, horizontal-flip, vertical-flip, zoom, brightness and shear. Such techniques to manipulate the images to obtain varying copies thereof for analysis purposes, in particular, to increase the number of images in the training image dataset, may be contemplated by a person skilled in the art and thus have not been explained in detail herein for the brevity of the present disclosure.

Figure 2:
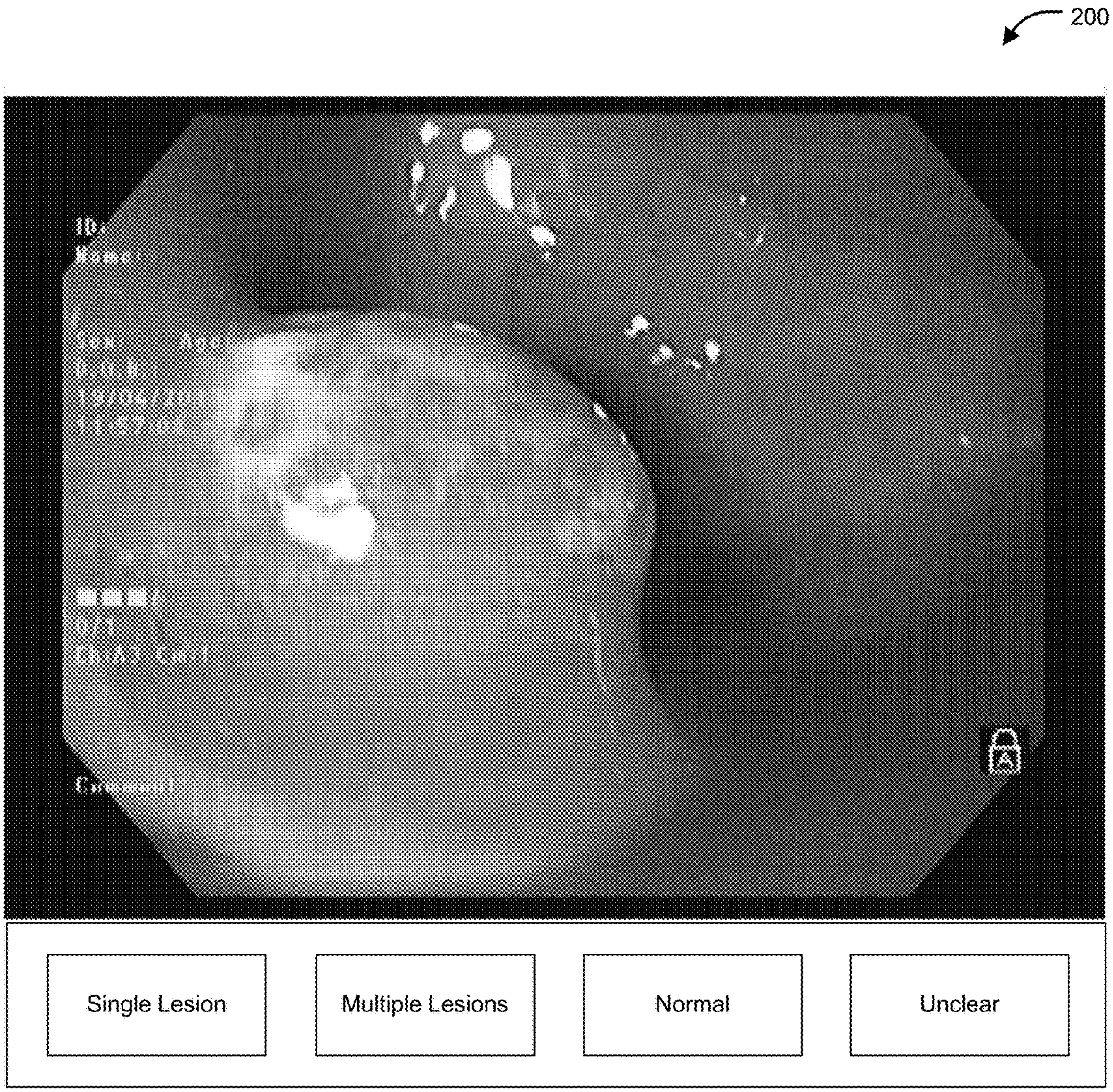
FIG. 2 illustrates a user interface to allow an operator to classify the plurality of medical images, in accordance with one or more exemplary embodiments of the present disclosure.

The received medical images may be filtered and cleaned, such that the positive images with polyps are separated from the negative images without polyps. For this purpose, a tool is provided (as seen in FIG. 2) to label the images. In particular, as shown in FIG. 2, the method 100 comprises providing a user interface 200 to allow an operator to classify each of the received plurality of medical images into one of: single lesion image with only one lesion, multiple lesions image with at least two lesions, normal image with no lesions and unclear image (e.g., blurry image). As may be seen, the user interface 200 displays the corresponding medical image of the plurality of medical images and provides options (in the form of buttons or the like) to label the displayed medical image into one of the at least four categories using the correspondingly provided buttons or the like therein. The user interface 200 may be a web interface that allows the operator to scan through the data and perform the classification task. For each medical image, the user interface 200 shows the endoscopy image, and allows the operator to select one out of the four classes. Once the labelling process is completed, the user interface 200 may automatically switch to the next medical image in the plurality of medical images, for further labelling purposes. It may be appreciated that the user interface 200 (as illustrated) is exemplary only, and shall not be construed as limiting to the present disclosure in any manner.

Figure 3:
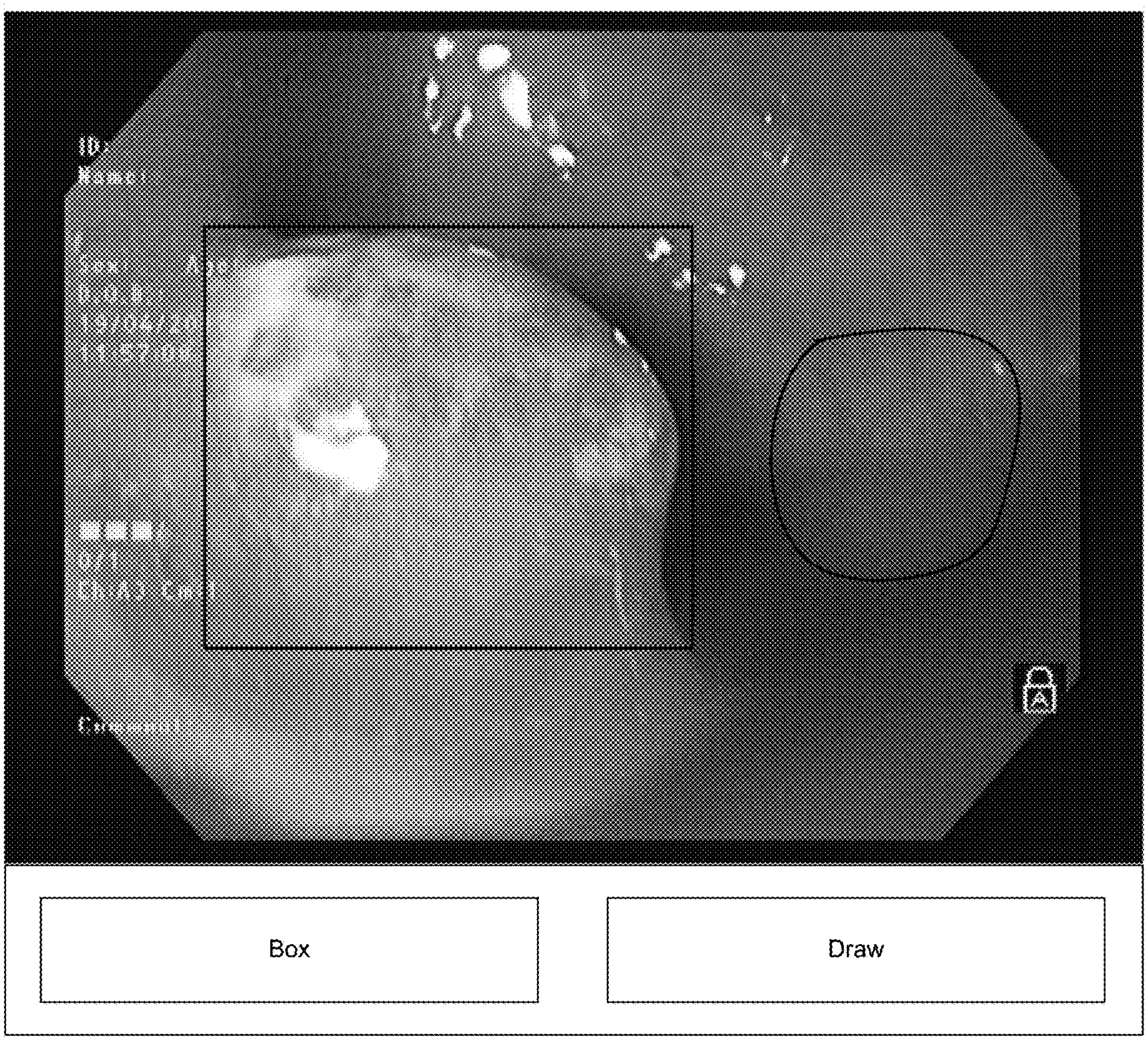
FIG. 3 illustrates a user interface to allow an operator to outline a bounding polygon on one or more lesions in each of the plurality of medical images, in accordance with one or more exemplary embodiments of the present disclosure.

In some embodiments, in case of the medical image being classified as the multiple lesions image, the method 100 further comprises labelling each of the multiple lesions in the corresponding medical image. FIG. 3 illustrates a user interface 300 to allow an operator to outline (draw) a bounding polygon on each of the at least two lesions in the multiple lesions image. The bounding polygon may be in the form of a box (rectangle) or may be drawn in a free-form manner by the operator, as desired. Such bounding polygon may provide indication for the lesion while processing the corresponding medical image, for further analysis. It may be appreciated that the user interface 300 (as illustrated) is exemplary only, and shall not be construed as limiting to the present disclosure in any manner.

Figure 4:
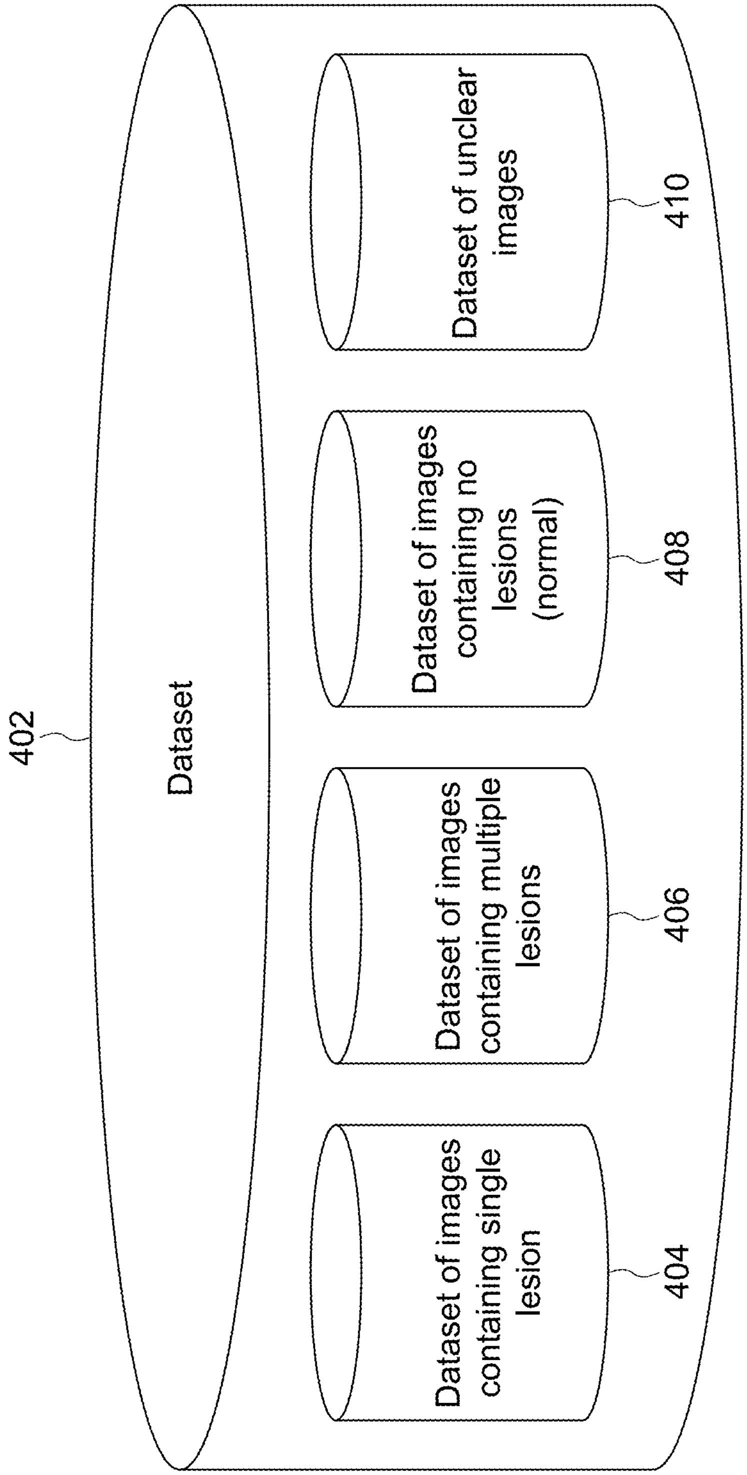
FIG. 4 illustrates a scheme for classification of medical images, in accordance with one or more exemplary embodiments of the present disclosure.

FIG. 4 illustrates a scheme 400 for classification of medical images, in accordance with one or more exemplary embodiments of the present disclosure. As shown, initially a dataset 402 of medical images is received. The dataset 402 may be sourced from medical institutes like hospitals, diagnostic laboratories, etc. The dataset 402 may be categorized into: publicly sourced data (which may be annotated), and private sourced data (which may generally be unannotated). The public sourced data includes datasets sourced from multiple publications. The private sourced data includes medical data sourced directly from hospitals across a region. It may be appreciated that both pools consisted of both negative as well as positive examples, i.e. images where polyps were present and not present. As shown in FIG. 4, each of the received plurality of medical images in the dataset 402 is classified into one of: a dataset 404 containing single lesion images, a dataset 406 containing multiple lesions image, a dataset 408 containing normal images and a dataset 410 containing unclear images. Further, the medical images may be classified as at least one of the single lesion image and the multiple lesions image are categorized as the positive images. It may be appreciated that when multiple operators are available, to reduce the burden on a single operator, the scheme 400 may divide the medical images among the various available operators. To gain more confidence in the classification, the scheme 400 may also allow for redundancy in which case any given image is classified by at least two operators.

Referring back to FIG. 1, at step 502, the method 100 comprises utilizing a trained segmentation model to generate a first segmentation mask for each of the one or more lesions in each of the medical images in the set of medical images. To build the segmentation model, a Fully Convolutional Network (FCN) may be used. An FCN has a series of Convolutional layers, and MaxPool layers with no fully connected layers. For the purposes of the present disclosure, the FCN implements the U-Net Architecture. The U-Net has an encoder-decoder styled architecture with special skip connections between the corresponding down-sampled and up-sampled counterparts. The proposed architecture makes use of a backbone network which serves as a feature extractor connected to the U-Net. The trained segmentation model is obtained by training a known segmentation model using a public data set. In general, such trained segmentation model may be capable of generating segmentation mask for 'single lesion images', as classified.

As discussed, in case of the medical image being classified as the multiple lesions image, a bounding polygon is outlined on each of the at least two lesions in the multiple lesions image. In such case, the method 100 comprises configuring the trained segmentation model (i.e. trained model as described above) to generate a sub-segmentation mask for each of the at least two lesions in the multiple lesions image. It may be appreciated that each of the lesions is identified using the respective bounding polygon, may be independently processed by the trained model for such purpose. Method 100 further comprises generating the segmentation mask for the multiple lesions image by union of the corresponding generated sub-segmentation masks. That is, the final segmentation mask (first segmentation mask) is obtained by combining the independently generated sub-segmentation mask for each of the at least two lesions in the multiple lesions image.

III. Geometric Filter

Referring again to FIG. 1, at step 504-510, the method 100 comprises implementing a geometric filter to validate if the generated first segmentation mask corresponds to the one or more lesions in the corresponding medical image based on geometric properties of the respective one or more lesions. It may be appreciated that when using the segmentation model trained on publicly available data sets to segment new private data sets, the implemented model may generate numerous false positive masks having irregular shapes. Polyps, on the other hand, typically have well defined regular shapes, mostly circular or elliptical (depending on the angle of the camera), and are relatively larger when compared to noisy false positives. With the use of geometric filter, it is made possible to use these well-defined geometric properties of the polyps to automatically filter out false positive masks, which can in turn be used to retrain and improve the segmentation model.

The geometric filter may validate the medical images (as received) with corresponding segmentation mask conforming to typical geometric properties of lesions (polyps). In the step of implementing the geometric filter, the method 100 comprises determining an area fraction. Further, the geometric filter may include determining one or more of: a relative area fraction, a convexity, an elliptical aspect ratio and an elliptical proximity. While a polyp does not contain holes, due to the segmentation model, a component can potentially have holes, in which case the current algorithm closes (or fills) the holes before computing the measures as described herein and further in the proceeding paragraphs.

The area fraction is based on a ratio of an area covered by each of the one or more lesions to a total area covered by other of one or more lesions for each of the plurality of medical images. This measure is computed as $$\frac{\text{area}(c)}{\sum_{c' \in C} area(c')}$$

the fraction of the area covered by the component with respect to the total area covered by all the components. Noise in the segmentation typically results in very small components, and this measure is used to filter out such spurious components (as discussed later in more detail).

The relative area fraction is based on a ratio of an area covered by each of the one or more lesions to a total area covered by a largest one component of other of one or more lesions for each of the plurality of medical images. This measure is computed as $$\frac{\text{area}(c)}{\max_{c' \in C}(area(c'))}$$

the fraction of the area covered by the component with respect to the area of the largest component. This measure is primarily used to handle cases wherein an image has multiple polyps. In such cases, the area fraction measure computed above will be significantly smaller than the single polyp case, and will not be an effective measure to characterize polyps.

The convexity is based on a ratio of an area covered by each of the one or more lesions to an area of a convex hull of the corresponding one of the one or more lesions. This measure is computed as $$\frac{\text{area}(c)}{\text{area}(ConvexHaull(c))}$$

the ratio between the area of the component with the area of the convex hull of the component. As polyps are typically complex, and the convexity allows us to identify potentially erroneous component segments.

The elliptical aspect ratio is based on a ratio of major axis to minor axis of an ellipse corresponding to each of the one or more lesions for each of the plurality of medical images. This measure is computed as $$\left(\frac{\text{major axis}}{\text{minor axis}}\right)$$

the ratio between major axis and minor axis of an elliptical structure of the component, which may be proxy to length and width of a minimum bounding rectangle that encompasses the given component. It is to be noted that this minimum bounding rectangle need not be axis-aligned. Such measure is used since it is expected that the polyp be "meatier".

The elliptical proximity is based on a ratio of perimeter of an elliptical structure with same area as an ellipse corresponding to each of the one or more lesions with major axis and minor axis thereof being equal to length and width respectively of a minimum bounding rectangle thereto in the corresponding medical image, to a perimeter of the ellipse corresponding to each of the one or more lesions in the corresponding medical image, for each of the plurality of medical images. This measure is computed as $$\frac{\text{perimeter}(e')}{\text{perimeter}(c)}$$

The closer the shape of a component is to being an ellipse, the closer the value of the elliptical proximity is to 1.

Further, the geometric filter may discard the medical image if the corresponding determined area fraction is less than a predefined threshold. That is, the geometric filter first uses the area fraction of the components to discard very small components (having area fraction <0.01). The method 100 further comprises implementing a regression function, trained based on ground truth values for relative area fraction, convexity, elliptical aspect ratio and elliptical proximity for lesions in medical images, to validate if the generated segmentation mask corresponds to the one or more lesions in the corresponding medical image of the plurality of medical images based on the determined relative area fraction, the determined convexity, the determined elliptical aspect ratio, and the determined elliptical proximity for lesions in the corresponding medical image. That is, using the ground truth masks from the public data, the regression function is trained based on the other four measures, namely relative area fraction, convexity, elliptical aspect ratio, and elliptical proximity. Some of the parameters of that regression function may be set to zero, effectively excluding one or more of the subcomputations from the final evaluation value of the geometric filter.

In particular, the present disclosure implements a logistic regression option provided by the "XGBoost" library for this purpose. It may use an ensemble of decision trees to learn and predict the classes, to classify if the properties of the shape correspond to a polyp or not. Training this model requires two classes of masks, those with valid polyps, and those that are not polyps. The valid polyp masks are obtained using the set of components from the public data set, while the set of masks that do not correspond to polyps consists of non-empty masks from the 'Normal images' as classified (described in the preceding paragraphs with reference to FIG. 4).

IV. Validation and Retraining of the Model

Figure 5:
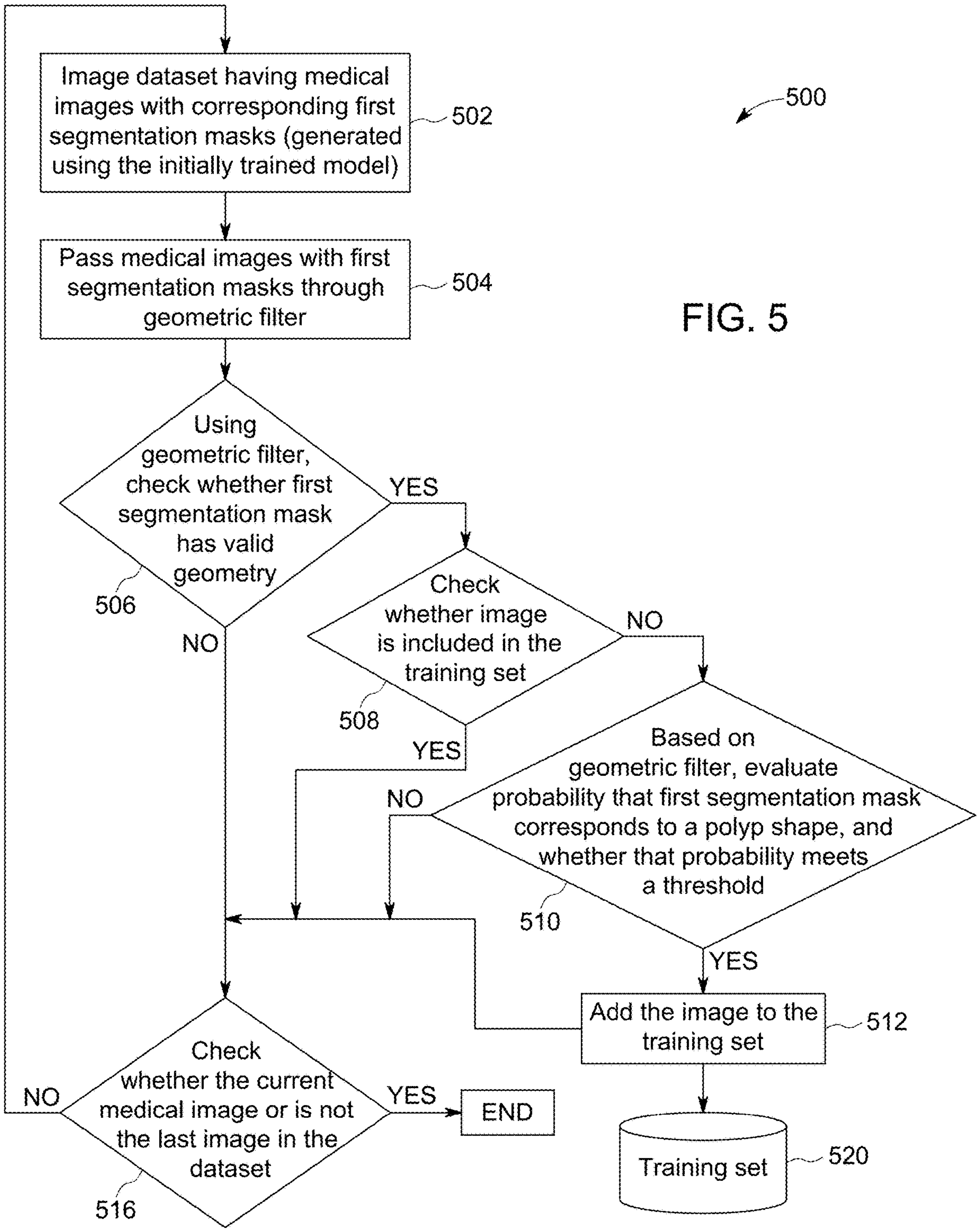
FIG. 5 illustrates a flowchart of a process depicting steps involved in implementation of a geometric filter to validate a generated segmentation mask, in accordance with one or more exemplary embodiments of the present disclosure.

Referring back to FIG. 1, based on the implementation of the geometric filter, at step 108, the method 100 further comprises updating the trained segmentation model using medical images with the validated first segmentation mask to obtain an updated segmentation model. FIG. 5 illustrates a flowchart of a process 500 depicting steps involved in implementation of a geometric filter to validate a generated segmentation mask, in accordance with one or more exemplary embodiments of the present disclosure. At step 502, an image dataset having medical images with corresponding first segmentation masks (generated using the initially trained model, as described in the preceding paragraph) is received. At step 504, the medical images with the corresponding first segmentation masks are passed through the present geometric filter. At step 506, the geometric filter is implemented to check if the first segmentation mask of a particular medical image has a valid geometry. If YES, at step 508, it is checked whether the particular image is included in the training set to be implemented. If YES, at step 510, it is checked if a probability of the given first segmentation mask corresponding to a polyp shape meets a defined threshold. Again, if YES, at step 512, the particular medical image is added to the training set 520. If NO for any of the above, the process 500 moves to step 514 to check the next medical image in the set of medical images. At step 516, a check is made if the current medical image being processed is not the last image in the dataset. If YES, the next image is processed as per the described steps. If NO, the training dataset is updated based on the obtained medical images with the corresponding validated segmentation masks.

Referring to FIG. 1, at step 110, the method 100 further comprises implementing the updated segmentation model to generate a second segmentation mask for each of the one or more lesions in the medical images in the set of medical images. Each of the medical images in the set of medical images may be processed using the updated segmentation model to generate the respective second segmentation mask thereafter. The process 500 (described in reference to FIG. 5) of identifying valid high-quality segmentation masks is then repeated using the updated segmentation model. Furthermore, for each medical image, the corresponding first segmentation mask is replaced by a second segmentation mask if the score of the geometric filter is higher for the second segmentation mask. This entire process is iteratively repeated until there are sufficient new high-quality images in the training set. The final model (i.e. the last updated segmentation model) is then used to generate masks for the other data classes, all of which are then validated by the experts to generate the required segmented images for training.

Figure 6:
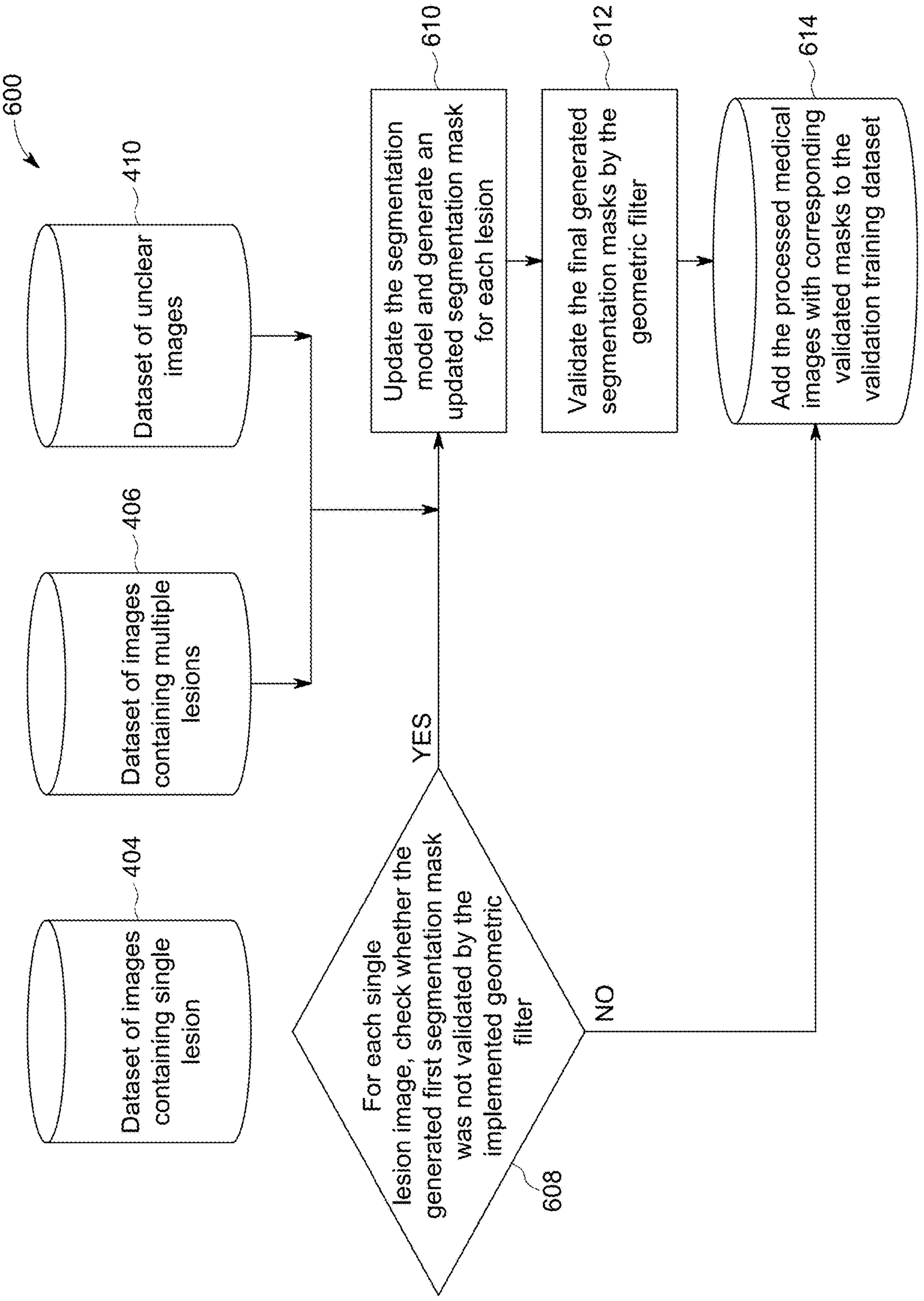
FIG. 6 illustrates a flowchart of a process depicting steps involved in generating a validated training dataset, in accordance with one or more exemplary embodiments of the present disclosure.

FIG. 6 illustrates a flowchart of a process depicting steps involved in generating a validated training dataset, in accordance with one or more exemplary embodiments of the present disclosure. Block 404 represents a dataset of single lesion images, block 406 represents a dataset of multiple lesions images, and block 410 represents a dataset of unclear images. At step 608, it is checked that for each single lesion image (from block 404) if the generated first segmentation mask was not validated by the implemented geometric filter. If NO, the particular single lesion image is added to a validation training dataset at step 614. If YES, the previously obtained updated segmentation model is implemented to generate a second segmentation mask for each of the one or more lesions for such single lesion images at step 610. Furthermore, the updated segmentation model is also implemented to generate segmentation mask for each of the one or more lesions the medical images from blocks 406, 410, at the step 610. As discussed, the final segmentation mask for such images is generated by union of the generated sub-segmentation masks for each of the one or more lesions therein. At step 612, the final generated segmentation masks are validated by the geometric filter. Finally, the processed medical images (in the step 612) with corresponding validated masks are added to the validation training dataset at the step 614.

In particular, for handling multiple lesions images, the present disclosure utilizes annotated images with each of the at least two lesions in the multiple lesions images with bounding box (or polygon), with none of the bounding boxes (or polygons) intersect (as described above). The probabilities of the mask restricted to each of bounding box is computed. To do this, for each bounding box, the regions outside the bounding box are concealed to generate a sub-mask. The geometric probability of the sub-mask being that of a (single) lesion is then evaluated. A mask is deemed to be valid if there is at least one sub-mask that passes the geometric filter. Then, a simple union of the masks that pass the geometric filter is performed. The union is straight forward as the bounding boxes (or polygons) do not intersect. Subsequently, the last probability of each of the sub-masks is fetched, and the geometric probability of the new sub-mask is compared with the existing sub-mask. Finally, a union of the best sub-masks is performed for each region and saved as the final mask for the image.

Referring again to FIG. 1, at step 112, the method 100 further comprises providing a user interface to allow an operator to validate last generated segmentation mask for each of the medical images in the set of medical images. With the process 600 (as described in reference to FIG. 6), the validation training dataset is obtained. The present disclosure provides that the medical images with the corresponding segmentation masks are validated by the operator, to be finally used as ground truth annotated dataset. The segmentation masks to be used for validation are decided based on the image class. For single lesion images, if the image and the corresponding mask were used as part of the intermediate training, then that mask is used. If not, the segmentation mask generated by the last trained model is used. For the multiple lesions images and unclear images, the mask generated by the last trained model is used. Further, the medical image along with the corresponding selected segmentation mask are displayed side-by-side, and the operator may simply confirm if the corresponding segmentation mask conforms to the respective medical image or not, for validation. Multiple operators may be assigned the task of validating medical images for faster results and to attain redundancy.

Figure 7:
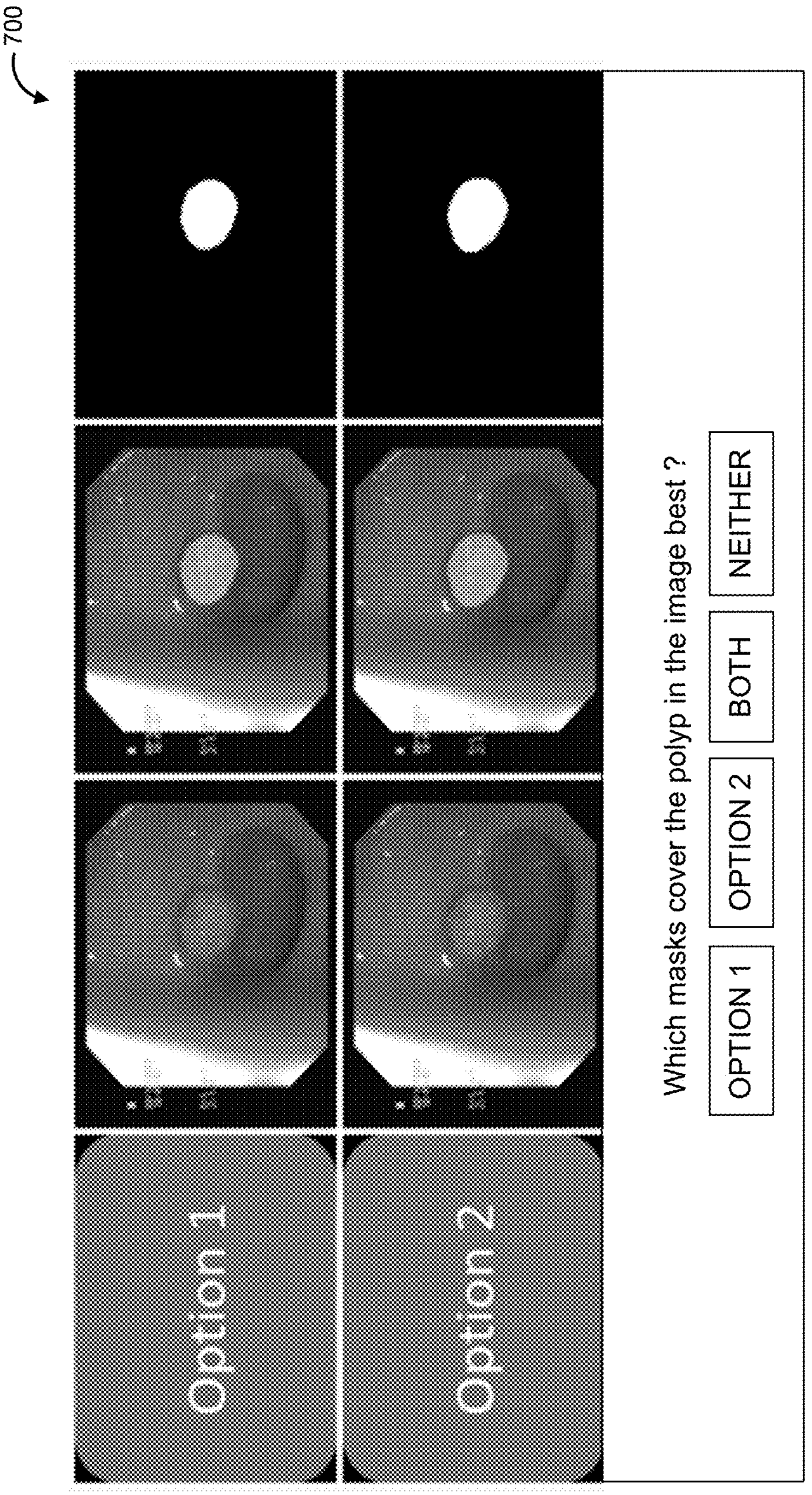
FIG. 7 illustrates a user interface to allow an operator to confirm one of segmentation masks based on close mapping thereof to one or more lesions in a corresponding medical image, in accordance with one or more exemplary embodiments of the present disclosure.

FIG. 7 illustrates a user interface 700 to allow an operator to confirm one of segmentation masks based on close mapping thereof to one or more lesions in a corresponding medical image, in accordance with a preferred embodiment of the present disclosure. In the preferred embodiment, the shown user interface 700 allows an operator to compare the first segmentation mask (as generated by initial segmentation model) and the last generated segmentation mask (either the first segmentation mask or the second segmentation mask) in consideration of the corresponding medical image, and to confirm one of the first segmentation mask and the last generated segmentation mask based on comparatively close mapping to the one or more lesions in the corresponding medical image of the plurality of medical images. In an embodiment, for the method 100, providing the user interface 700 comprises configuring the user interface 700 to allow the operator to confirm one of the first segmentation mask and the last generated segmentation mask by using a single action. For example, as illustrated, the user interface 700, which may be a web interface, allows the operator to simply select one of the options from the first segmentation mask and the last generated segmentation mask by clock of a button or the like, in order to make the process fast, simple and reliable.

Referring again to FIG. 1, at step 114, the method 100 comprises selecting the medical images from the plurality of medical images with the validated generated segmentation mask, to generate a ground truth annotated dataset. The medical images from the plurality of medical images with confirmation that the respective generated segmentation mask having comparatively closed mapping to the one or more lesions therein are selected to be included in the ground truth annotated dataset. Such ground truth annotated dataset may then be utilized for machine learning implementation (i.e. training of a machine learning model) for segmenting lesions in medical images.

Figure 8:
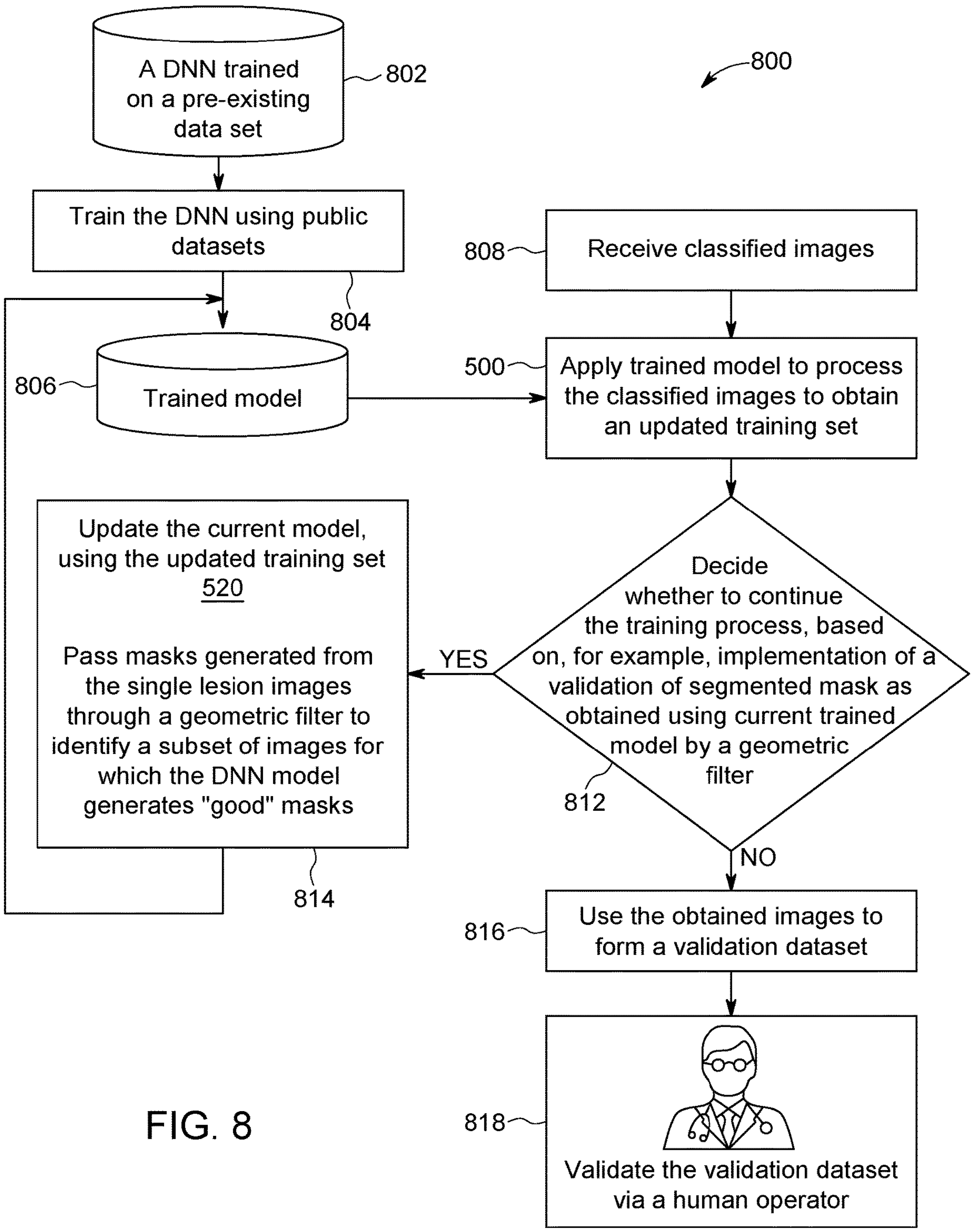
FIG. 8 illustrates a flowchart of a process depicting steps involved in generating ground truth annotated dataset for machine learning implementation for segmenting lesions in medical images, in accordance with one or more exemplary embodiments of the present disclosure.

As discussed, the present disclosure aims to significantly reduce the burden on human experts in the process of generating high quality segmented data that can be used for training new deep neural networks (DNNs). Given a data set from a new source, the process to generate new training data is described in reference to FIG. 8. FIG. 8 illustrates a flowchart of a process 800 depicting steps involved in generating ground truth annotated dataset for machine learning implementation for segmenting lesions in medical images, in accordance with one or more exemplary embodiments of the present disclosure. As shown in FIG. 8, at block 802, first a DNN with "NULL" training is provided. At block 804, the DNN is trained using the public datasets. At block 806, a trained model is obtained. Such trained model is implemented for generating a first segmentation mask for each of the one or more lesions in each of the medical images in the set of medical images.

On the other hand, as discussed in description of FIG. 4, first the images in the dataset 402 are segregated into 4 classes: a dataset 404 containing single lesion images, a dataset 406 containing multiple lesions image, a dataset 408 containing normal images and a dataset 410 containing unclear (ambiguous) images. In the process 800 of FIG. 8, the classified images are received at block 808. At block 500, the trained model (from block 806) is implemented to process the classified images to obtain an updated training set. At block 812, a decision is made on whether to continue the training process. Such decision may be based on implementation of a validation of segmented mask as may be obtained using current trained model by a geometric filter (as discussed in the proceeding paragraphs).

If YES, at block 814, the current model is updated using the updated training set. In particular, the masks generated from the single lesion image are passed through a geometric filter to identify a subset of images for which the DNN model generates "good" masks. These images and masks are then added as part of the training data, and a new model is trained. The above process of identifying good masks is then repeated using the new model. This process is repeated until there are sufficient new images in the training set. If NO, at block 816, the obtained images are used to form a validation dataset. At block 818, the validation dataset is validated by an operator, which in turn may be used to select the medical images from the plurality of medical images to be included in the ground truth annotated dataset.

In one or more embodiments, the method 100 further comprises varying one or more weighted parameters of the implemented regression function to manipulate validation of the generated segmentation mask. It may be noted that the segmentation model obtained by the described method 100 (process 800) depends on the geometric filter. A conservative filter might end up filtering out a lot of medium quality mask, while a more liberal filter could allow spurious masks. Since, the filter itself is a heuristic, the above data generation process may be performed using both a conservative filter and a liberal (over-fitted) filter by appropriately varying the parameters of used regression function. Thus, for each medical image that has one or more lesions, the method 100 (process 800) may generate three segmentation masks, one generated using the initial model trained using the public data sets, and two masks generated using the iterative process, one using the conservative filter, and one using the liberal filter. Each of the generated three segmentation masks are provided as options to the operator in the user interface 700, to allow the expert operator to select a valid one to be included in the ground truth annotated dataset.

Figure 9A:
FIGS. 9A-9K are exemplary medical images with lesions that could be detected by utilizing the machine learning implementation using the generated ground truth annotated dataset, in accordance with one or more exemplary embodiments of the present disclosure.
Figure 9B:
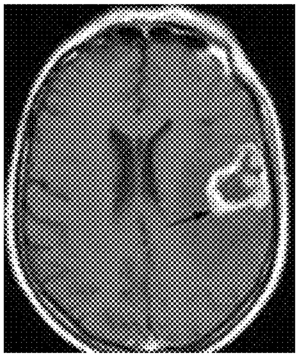
Figure 9C:

FIGS. 9A-9N are exemplary medical images with lesions that could be detected by utilizing the machine learning implementation using the generated ground truth annotated dataset, in accordance with one or more exemplary embodiments of the present disclosure. In particular, FIG. 9A depicts a multiple sclerosis lesion as obtained from a brain MRI scan. FIG. 9B depicts a lesion related to brain tumour as obtained from a brain MRI scan. FIG. 9C depicts a lesion related to hydatid cyst as obtained from a brain MRI scan.

Figure 9D:
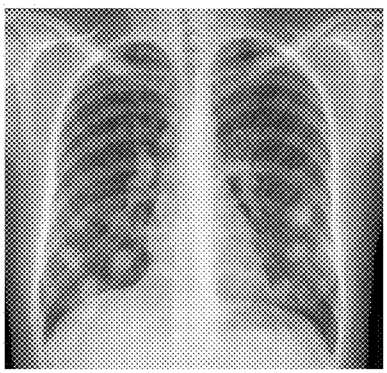
Figure 9E:
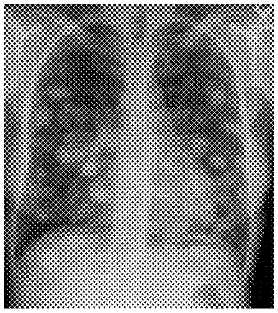
Figure 9F:
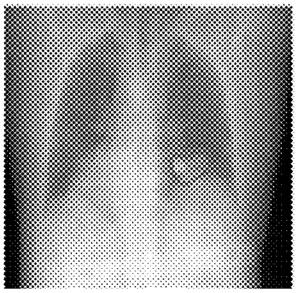
Figure 9G:
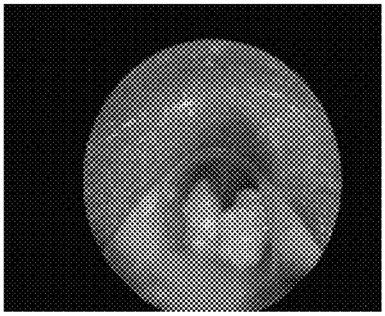
Figure 9H:
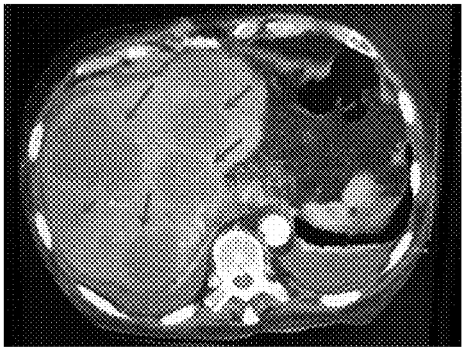
Figure 9I:
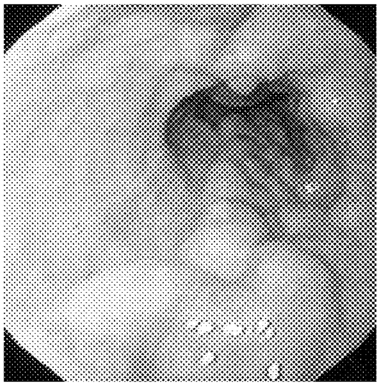
Figure 9J:
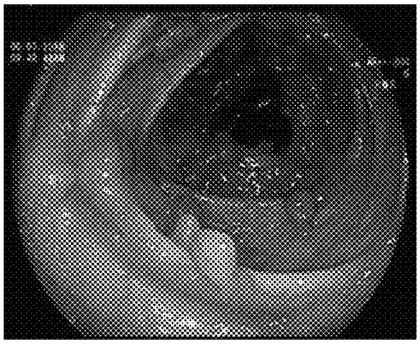
Figure 9K:
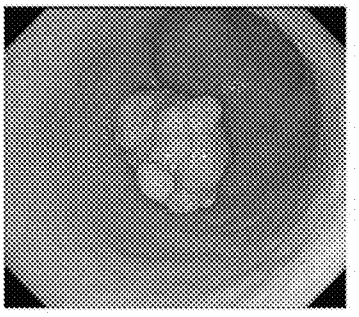

FIG. 9D depicts a cystic lesion as obtained from an X-ray scan. FIG. 9E depicts lesions related to pulmonary nodules as obtained from X-ray scan. FIG. 9F depicts lesions related to lung tumour as obtained from X-ray scan. FIG. 9G depicts lesions related to lung tumour as obtained from bronchoscopy. FIG. 9H depicts lesion related to hepatic metastases and lymphoma as obtained from liver scans. FIG. 9I depicts lesion related to gastric varices as obtained from GI tract endoscopy scans. FIG. 9J depicts lesion related to gastric/colonic polyps as obtained from GI tract endoscopy scans. FIG. 9K depicts lesion related to gastric/colonic cancer as obtained from GI tract endoscopy scans. All such lesions may be detected by utilizing the machine learning model trained using the generated ground truth annotated dataset, which may be implemented by the clinical decision support system as descried above.

Figure 10:
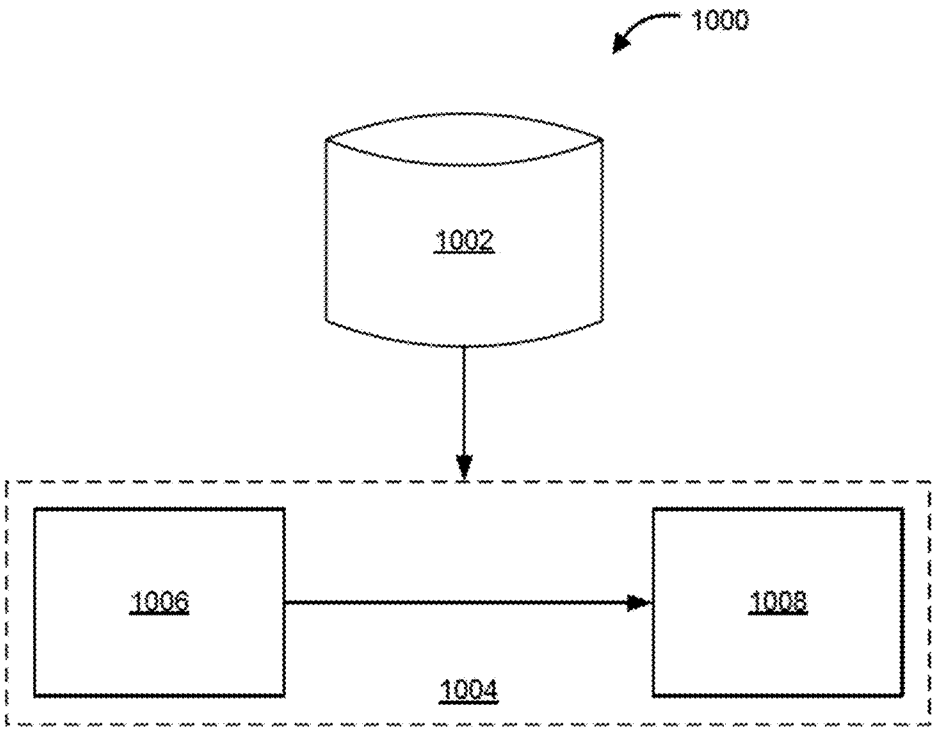
FIG. 10 illustrates a block diagram representation of a system for semi-automatically generating annotated dataset for machine learning implementation for segmenting lesions in medical images, in accordance with one or more exemplary embodiments of the present disclosure.

The present disclosure further provides a system for semi-automatically generating annotated dataset for machine learning implementation for segmenting lesions in medical images. The various embodiments and variants disclosed above apply mutatis *mutandis* to the present system. FIG. 10 illustrates a block diagram representation of a system 1000 for semi-automatically generating annotated dataset for machine learning implementation for segmenting lesions in medical images, in accordance with one or more exemplary embodiments of the present disclosure. The system 1000 includes a memory arrangement 1002 configured to receive a plurality of medical images corresponding to regions with possible one or more lesions, with a set of medical images of the plurality of medical images being categorized into positive images having one or more lesions. The system 1000 further include a processing arrangement 1004 configured to: utilize a trained segmentation model (in the form of a module 1006) to generate a first segmentation mask 1008 for each of the one or more lesions in each of the medical images in the set of medical images; implement a geometric filter (in the form of a module 1008) to validate if the generated first segmentation mask corresponds to the one or more lesions in the corresponding medical image based on geometric properties of the respective one or more lesions; update the trained segmentation model using medical images with the validated first segmentation mask to obtain an updated segmentation model; implement the updated segmentation model to generate a second segmentation mask for each of the one or more lesions in the medical images in the set of medical images; provide a user interface to allow an operator to validate the last generated segmentation mask for each of the medical images in the set of medical images; and select the medical images from the plurality of medical images with the validated generated segmentation mask, to generate a ground truth annotated dataset.

The present disclosure further provides a machine learning model trained using the generated ground truth annotated dataset (as discussed in the preceding paragraphs) for diagnosis of lesions from medical images. The present disclosure further provides a clinical decision support system implementing the machine learning model to support a medical practitioner in diagnosis of lesions from medical images. A machine learning model may include a model developed based software algorithms that can improve performance of the model by one or more training procedures implemented by a computer without the computer having to be explicitly programmed based on the data. For example, neural networks techniques, support vector machine techniques can be used for implementing the machine learning model. However, other embodiments could utilize one or more of available machine learning algorithms.

Figure 11:
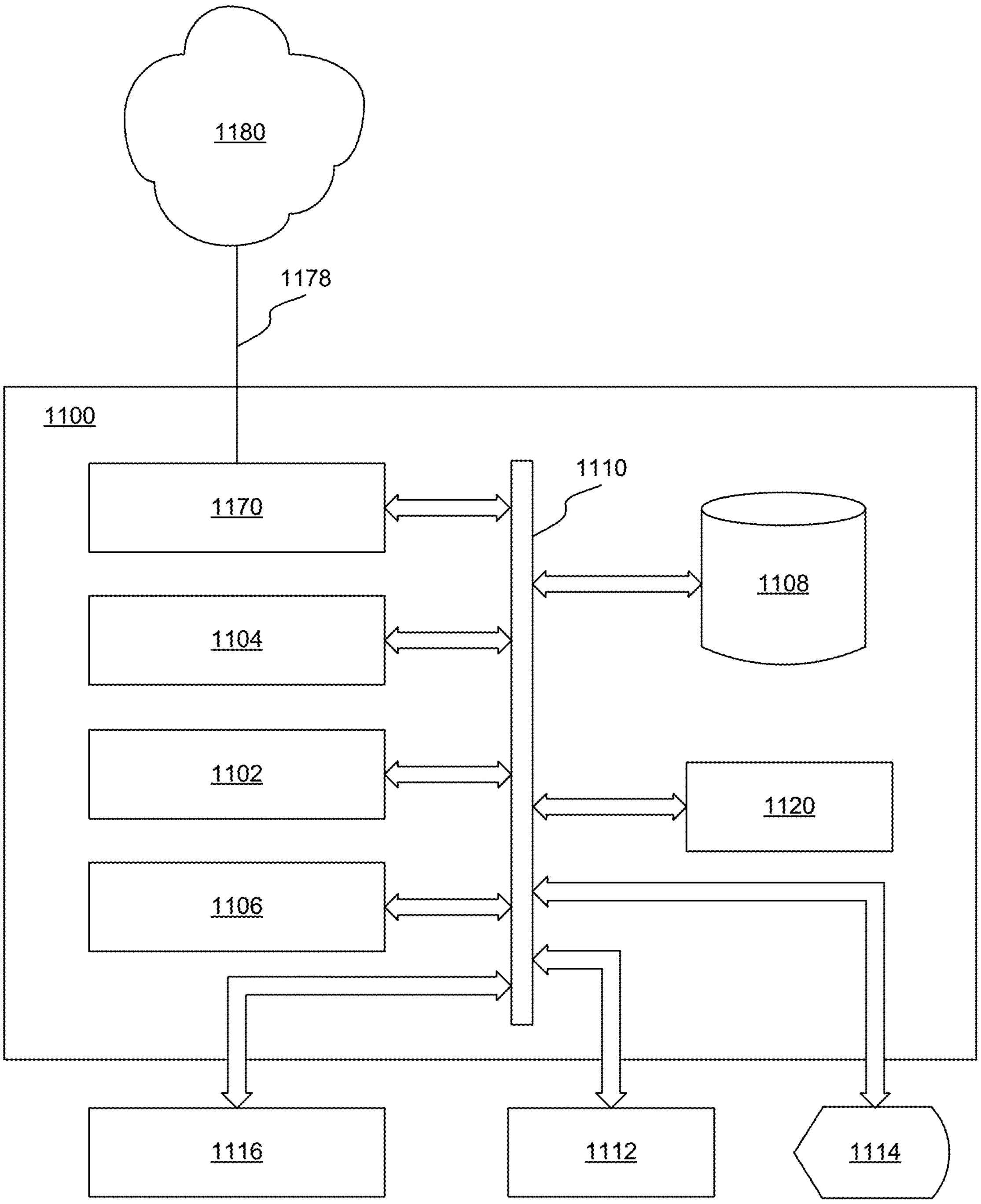
FIG. 11 is a schematic representation of a computing hardware that can be used to implement the present system, in accordance with one or more exemplary embodiments of the present disclosure.

FIG. 11 is a schematic representation of a computing hardware 1100 that can be used to implement the present system, in accordance with one or more exemplary embodiments of the present disclosure. Computing hardware 1100 is programmed (e.g., via computer program code or instructions) to semi-automatically generate ground truth annotated dataset for machine learning implementation for segmenting lesions in medical images as described herein and includes a communication mechanism such as a bus 1110 for passing information between other internal and external components of the computing hardware 1100. Information (also called data) is represented as a physical expression of a measurable phenomenon, typically electric voltages, but including, in other embodiments, such phenomena as magnetic, electromagnetic, pressure, chemical, biological, molecular, atomic, sub-atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range.

A bus 1110 includes one or more parallel conductors of information so that information is transferred quickly among devices coupled to the bus 1110. One or more processors 1102 for processing information are coupled with the bus 1110.

A processor 1102 performs a set of operations on information as specified by computer program code related to generating ground truth annotated dataset. The computer program code is a set of instructions or statements providing instructions for the operation of the processor and/or the computer system to perform specified functions. The code, for example, may be written in a computer programming language that is compiled into a native instruction set of the processor. The code may also be written directly using the native instruction set (e.g., machine language). The set of operations include bringing information in from the bus 1110 and placing information on the bus 1110. The set of operations also typically include comparing two or more units of information, shifting positions of units of information, and combining two or more units of information, such as by addition or multiplication or logical operations like OR, exclusive OR (XOR), and N. Each operation of the set of operations that can be performed by the processor is represented to the processor by information called instructions, such as an operation code of one or more digits. A sequence of operations to be executed by the processor 1102, such as a sequence of operation codes, constitute processor instructions, also called computer system instructions or, simply, computer instructions. Processors may be implemented as mechanical, electrical, magnetic, optical, chemical or quantum components, among others, alone or in combination.

Computing hardware 1100 also includes a memory 1104 coupled to bus 1110. The memory 1104, such as a random-access memory (RAM) or other dynamic storage device, stores information including processor instructions for generating ground truth annotated dataset. Dynamic memory allows information stored therein to be changed by the computing hardware 1100. RAM allows a unit of information stored at a location called a memory address to be stored and retrieved independently of information at neighboring addresses. The memory 1104 is also used by the processor 1102 to store temporary values during execution of processor instructions. The computing hardware 1100 also includes a read only memory (ROM) 1106 or other static storage device coupled to the bus 1110 for storing static information, including instructions, that is not changed by the computing hardware 1100. Some memory is composed of volatile storage that loses the information stored thereon when power is lost. Also coupled to bus 1110 is a non-volatile (persistent) storage device 1108, such as a magnetic disk, optical disk or flash card, for storing information, including instructions, that persists even when the computing hardware 1100 is turned off or otherwise loses power.

Information, including instructions for generating ground truth annotated dataset, is provided to the bus 1110 for use by the processor from an external input device 1112, such as a keyboard containing alphanumeric keys operated by a human user, or a sensor. A sensor detects conditions in its vicinity and transforms those detections into physical expression compatible with the measurable phenomenon used to represent information in computing hardware 1100. Other external devices coupled to bus 1110, used primarily for interacting with humans, include a display device 1114, such as a cathode ray tube (CRT) or a liquid crystal display (LCD), or plasma screen or printer for presenting text or images, and a pointing device 1116, such as a mouse or a trackball or cursor direction keys, or motion sensor, for controlling a position of a small cursor image presented on the display 1114 and issuing commands associated with graphical elements presented on the display 1114. In some embodiments, for example, in embodiments in which the computing hardware 1100 performs all functions automatically without human input, one or more of external input device 1112, display device 1114 and pointing device 1116 is omitted.

In the illustrated embodiment, special purpose hardware, such as an application specific integrated circuit (ASIC) 1120, is coupled to bus 1110. The special purpose hardware is configured to perform operations not performed by processor 1102 quickly enough for special purposes. Examples of application specific ICs include graphics accelerator cards for generating images for display 1114, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computing hardware 1100 also includes one or more instances of a communications interface 1170 coupled to bus 1110. Communication interface 1170 provides a one-way or two-way communication coupling to a variety of external devices that operate with their own processors, such as printers, scanners and external disks. In general, the coupling is with a network link 1178 that is connected to a local network 1180 to which a variety of external devices with their own processors are connected. For example, communication interface 1170 may be a parallel port or a serial port or a universal serial bus (USB) port on a personal computer. In some embodiments, communications interface 1170 is an integrated services digital network (ISDN) card or a digital subscriber line (DSL) card or a telephone modem that provides an information communication connection to a corresponding type of telephone line. In some embodiments, a communication interface 1170 is a cable modem that converts signals on bus 1110 into signals for a communication connection over a coaxial cable or into optical signals for a communication connection over a fiber optic cable. As another example, communications interface 1170 may be a local area network (LAN) card to provide a data communication connection to a compatible LAN, such as Ethernet. Wireless links may also be implemented. For wireless links, the communications interface 1170 sends or receives or both sends and receives electrical, acoustic or electromagnetic signals, including infrared and optical signals, that carry information streams, such as digital data. For example, in wireless handheld devices, such as mobile telephones like cell phones, the communications interface 1170 includes a radio band electromagnetic transmitter and receiver called a radio transceiver. In certain embodiments, the communications interface 1170 enables connection to the local network 1180.

A computer-readable medium may be any medium that participates in providing information to processor 1102, including instructions for execution. Non-volatile media include, for example, optical or magnetic disks, such as storage device 1108. Volatile media include, for example, dynamic memory 1104. Transmission media include, for example, coaxial cables, copper wire, fiber optic cables, and carrier waves that travel through space without wires or cables, such as acoustic waves and electromagnetic waves, including radio, optical and infrared waves. Signals include man-made transient variations in amplitude, frequency, phase, polarization or other physical properties transmitted through the transmission media. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, an EPROM, a FLASH-EPROM, any other memory chip or cartridge, a carrier wave, or any other medium from which a computer can read.

The problem of disease detection or segmentation has been previously solved for modalities like optical endoscopy, wireless capsule endoscopy and CT and MR virtual endoscopy using convolutional neural networks along with several pre-processing and post-processing interventions. However, the method of data annotation using novel semi-automated human-in-the-loop approach in conjunction with computational geometric techniques as described in the embodiments of the present disclosure provides significant advantages over the known techniques. Experiments demonstrated that the present approach not only generated high quality annotations but also significantly reduces the time imposed on the experts. In one experiment, the present approach managed to annotate over 60% of the images in the quantitative experiment using public data sets, and 69% in the local data. While having a higher number is preferable, in terms of absolute numbers (e.g., 674 in case of the local data set), this is sufficiently high for training new models.

The foregoing descriptions of specific embodiments of the present disclosure have been presented for purposes of illustration and description. They are not intended to be exhaustive or to limit the present disclosure to the precise forms disclosed, and obviously many modifications and variations are possible in light of the above teaching. The exemplary embodiment was chosen and described in order to best explain the principles of the present disclosure and its practical application, to thereby enable others skilled in the art to best utilize the present disclosure and various embodiments with various modifications as are suited to the particular use contemplated.

Various processes described herein may be implemented by appropriately programmed general purpose computers, special purpose computers, and computing devices. Typically a processor (e.g., one or more microprocessors, one or more microcontrollers, one or more digital signal processors) will receive instructions (e.g., from a memory or like device), and execute those instructions, thereby performing one or more processes defined by those instructions. Instructions may be embodied in one or more computer programs, one or more scripts, or in other forms. The processing may be performed on one or more microprocessors, central processing units (CPUs), computing devices, microcontrollers, digital signal processors, or like devices or any combination thereof. Programs that implement the processing, and the data operated on, may be stored and transmitted using a variety of media. In some cases, hard-wired circuitry or custom hardware may be used in place of, or in combination with, some or all of the software instructions that can implement the processes. Algorithms other than those described may be used.

Programs and data may be stored in various media appropriate to the purpose, or a combination of heterogeneous media that may be read and/or written by a computer, a processor or a like device. The media may include non-volatile media, volatile media, optical or magnetic media, dynamic random access memory (DRAM), static ram, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge or other memory technologies. Transmission media include coaxial cables, copper wire and fiber optics, including the wires that comprise a system bus coupled to the processor.

Databases may be implemented using database management systems or ad hoc memory organization schemes. Alternative database structures to those described may be readily employed. Databases may be stored locally or remotely from a device which accesses data in such a database.

In some cases, the processing may be performed in a network environment including a computer that is in communication (e.g., via a communications network) with one or more devices. The computer may communicate with the devices directly or indirectly, via any wired or wireless medium (e.g. the Internet, LAN, WAN or Ethernet, Token Ring, a telephone line, a cable line, a radio channel, an optical communications line, commercial on-line service providers, bulletin board systems, a satellite communications link, a combination of any of the above). Each of the devices may themselves comprise computers or other computing devices, such as those based on the Intel® Pentium® or Centrino™ processor, that are adapted to communicate with the computer. Any number and type of devices may be in communication with the computer.

A server computer or centralized authority may or may not be necessary or desirable. In various cases, the network may or may not include a central authority device. Various processing functions may be performed on a central authority server, one of several distributed servers, or other distributed devices.

The invention claimed is:

1. A method, comprising the steps of:

to images of a plurality of medical images, applying a trained segmentation model to generate first segmentation masks for lesions of the medical images, a segmentation mask being a designation of an area of an image corresponding to a lesion shown in the image, a segmentation model being an artificial intelligence model trained to identify segmentation masks corresponding to lesions in medical images;

applying a geometric filter to evaluate the generated first segmentation masks based on geometric properties of the respective one or more lesions in the images;

combining into a training set for training of a segmentation model the evaluated first segmentation masks and their corresponding images based at least in part on meeting the geometric filter; and training a regression function based on ground truth values for relative area fraction, convexity, elliptical aspect ratio and elliptical proximity for lesions in medical images, to validate if the generated segmentation mask corresponds to the one or more lesions in the corresponding medical image.

2. The method of claim 1, wherein in the applied geometric filter includes at least:

determining an area fraction based on a ratio of an area covered by one or more lesions to a total area covered by other of one or more lesions.

3. The method of claim 1, wherein in the applied geometric filter includes one or more of:

a relative area fraction based on a ratio of an area covered by each of the one or more lesions to a total area covered by a largest one component of other of one or more lesions for each of the plurality of medical images;

a convexity based on a ratio of an area covered by each of the one or more lesions to an area of a convex hull of the corresponding one of the one or more lesions;

an elliptical aspect ratio based on a ratio of major axis to minor axis of an ellipse corresponding to one or more lesions of the plurality of medical images; and an elliptical proximity based on a ratio of perimeter of an elliptical structure with same area as an ellipse corresponding to each of the one or more lesions with major axis and minor axis thereof being equal to length and width respectively of a minimum bounding rectangle thereto in the corresponding medical image, to a perimeter of the ellipse corresponding to each of the one or more lesions in the corresponding medical image.

4. The method of claim 3, wherein in the applied geometric filter includes one or more of:

a relative area fraction based on a ratio of an area covered by each of the one or more lesions to a total area covered by a largest one component of other of one or more lesions for each of the plurality of medical images;

a convexity based on a ratio of an area covered by each of the one or more lesions to an area of a convex hull of the corresponding one of the one or more lesions; and an elliptical aspect ratio based on a ratio of major axis to minor axis of an ellipse corresponding to one or more lesions of the plurality of medical images.

5. The method of claim 1, wherein in the applied geometric filter includes at least two of:

determining an area fraction based on a ratio of an area covered by one of the lesions to a total area covered by other of one or more lesions or all lesions of the corresponding medical image;

a relative area fraction based on a ratio of an area covered by one of the lesions to a total area covered by a largest component of other of one or more lesions of the corresponding medical image;

a convexity based on a ratio of an area covered by a lesions to an area of a convex hull of the lesion; and an elliptical aspect ratio based on a ratio of major axis to minor axis of an ellipse corresponding to a lesion.

6. The method of claim 1, wherein in the applied geometric filter includes at least three of:

determining an area fraction based on a ratio of an area covered by one of the lesions to a total area covered by other of one or more lesions or all lesions of the corresponding medical image;

a relative area fraction based on a ratio of an area covered by one of the lesions to a total area covered by a largest component of other of one or more lesions of the corresponding medical image;

a convexity based on a ratio of an area covered by a lesions to an area of a convex hull of the lesion; and an elliptical aspect ratio based on a ratio of major axis to minor axis of an ellipse corresponding to a lesion.

7. The method of claim 1, further comprising the step of:

at a user interface, receiving data from an operator to classify images of the plurality of medical images into one of: single lesion image with only one lesion, multiple lesion image with at least two lesions, normal image with no lesions, and unclear images.

8. The method of claim 1, further comprising the step of:

based on the evaluation of the geometric filter, discarding the medical image from the training set.

9. The method of claim 1, further comprising the step of:

varying one or more weighted parameters of the regression function to manipulate validation of the generated segmentation mask.

10. The method of claim 1, further comprising the step of:

augmenting a number of medical images in the plurality of medical images by using one or more techniques of: rotate, width-shift, horizontal-shift, horizontal-flip, vertical-flip, zoom, brightness and shear.

11. The method of claim 1, further comprising the step of:

at a user interface, obtaining from a human operator a confirmation of segmentation masks to incorporate images and segmentation masks into an augmented training set for training of the segmentation model.

12. A machine-readable, non-transitory memory, having stored thereon one or more programs programmed to cause a processor to compute at least the following:

to images of a plurality of medical images, to apply a trained segmentation model to generate first segmentation masks for lesions of the medical images, a segmentation mask being a designation of an area of an image corresponding to a lesion shown in the image, a segmentation model being an artificial intelligence model trained to identify segmentation masks corresponding to lesions in medical images;

to apply a geometric filter to evaluate the generated first segmentation masks based on geometric properties of the respective one or more lesions in the images;

to combine into a training set for training of a segmentation model the evaluated first segmentation masks and their corresponding images based at least in part on meeting the geometric filter; and to train a regression function based on ground truth values for relative area fraction, convexity, elliptical aspect ratio, and elliptical proximity for lesions in medical images, to validate if the generated segmentation mask corresponds to the one or more lesions in the corresponding medical image.

13. The memory of claim 12, wherein in the applied geometric filter includes one or more of:

determining an area fraction based on a ratio of an area covered by one or more lesions to a total area covered by other of one or more lesions;

a relative area fraction based on a ratio of an area covered by each of the one or more lesions to a total area covered by a largest one component of other of one or more lesions for each of the plurality of medical images;

a convexity based on a ratio of an area covered by each of the one or more lesions to an area of a convex hull of the corresponding one of the one or more lesions;

an elliptical aspect ratio based on a ratio of major axis to minor axis of an ellipse corresponding to one or more lesions of the plurality of medical images; and an elliptical proximity based on a ratio of perimeter of an elliptical structure with same area as an ellipse corresponding to each of the one or more lesions with major axis and minor axis thereof being equal to length and width respectively of a minimum bounding rectangle thereto in the corresponding medical image, to a perimeter of the ellipse corresponding to each of the one or more lesions in the corresponding medical image.

14. The memory of claim 12, wherein in the applied geometric filter includes at least two of:

determining an area fraction based on a ratio of an area covered by one of the lesions to a total area covered by other of one or more lesions or all lesions of the corresponding medical image;

a relative area fraction based on a ratio of an area covered by one of the lesions to a total area covered by a largest component of other of one or more lesions of the corresponding medical image;

a convexity based on a ratio of an area covered by a lesions to an area of a convex hull of the lesion; and an elliptical aspect ratio based on a ratio of major axis to minor axis of an ellipse corresponding to a lesion.

15. The memory of claim 12, wherein in the applied geometric filter includes at least three of:

determining an area fraction based on a ratio of an area covered by one of the lesions to a total area covered by other of one or more lesions or all lesions of the corresponding medical image;

a relative area fraction based on a ratio of an area covered by one of the lesions to a total area covered by a largest component of other of one or more lesions of the corresponding medical image;

a convexity based on a ratio of an area covered by a lesions to an area of a convex hull of the lesion; and an elliptical aspect ratio based on a ratio of major axis to minor axis of an ellipse corresponding to a lesion.

16. The memory of claim 12, further having stored thereon one or more programs programmed to cause the processor:

to discard, based on the evaluation of the geometric filter, the medical image from the training set.

17. The memory of claim 12, further having stored thereon one or more programs programmed to cause the processor:

to vary one or more weighted parameters of the regression function to manipulate validation of the generated segmentation mask.

18. A method, comprising the steps of:

to images of a plurality of medical images, applying a trained segmentation model to generate first segmentation masks for lesions of the medical images, a segmentation mask being a designation of an area of an image corresponding to a lesion shown in the image, a segmentation model being an artificial intelligence model trained to identify segmentation masks corresponding to lesions in medical images;

applying a geometric filter to evaluate the generated first segmentation masks based on geometric properties of the respective one or more lesions in the images; and combining into a training set for training of a segmentation model the evaluated first segmentation masks and their corresponding images based at least in part on meeting the geometric filter;

wherein in the applied geometric filter includes at least four of:

determining an area fraction based on a ratio of an area covered by one of the lesions to a total area covered by other of one or more lesions or all lesions of the corresponding medical image;

a relative area fraction based on a ratio of an area covered by one of the lesions to a total area covered by a largest component of other of one or more lesions of the corresponding medical image;

a convexity based on a ratio of an area covered by a lesions to an area of a convex hull of the lesion; and an elliptical aspect ratio based on a ratio of major axis to minor axis of an ellipse corresponding to a lesion.

* * * * *